United States Patent [19]
Clift et al.

[11] Patent Number: 6,051,595
[45] Date of Patent: Apr. 18, 2000

[54] METHOD FOR CONTROLLING FLIES INFESTING MUSHROOMS BY USING A N-ARYLPYRAZOLE OR A N-HETEROARYLPYRAZOLE COMPOUND

[75] Inventors: Alan Donald Clift; Maryann Terras, both of New South Wales, Australia

[73] Assignee: Rhone-Poulenc Agro, Lyons, France

[21] Appl. No.: 08/973,270

[22] PCT Filed: May 30, 1996

[86] PCT No.: PCT/EP96/02317

§ 371 Date: Apr. 2, 1998

§ 102(e) Date: Apr. 2, 1998

[87] PCT Pub. No.: WO96/38044

PCT Pub. Date: Dec. 5, 1996

[30] Foreign Application Priority Data

May 31, 1995 [AU] Australia .................. PN 3283

[51] Int. Cl.[7] .................. A01N 43/40; A01N 43/56
[52] U.S. Cl. .................. 514/404; 514/333; 514/407
[58] Field of Search .................. 514/404, 407, 514/333

[56] References Cited

U.S. PATENT DOCUMENTS

| | | | |
|---|---|---|---|
| 5,232,940 | 8/1993 | Hatton et al. | 514/407 |
| 5,236,938 | 8/1993 | Huang et al. | 514/341 |
| 5,306,694 | 4/1994 | Phillips et al. | 504/253 |
| 5,512,279 | 4/1996 | Jarrett et al. | 424/93.461 |

FOREIGN PATENT DOCUMENTS

| | | |
|---|---|---|
| 0295117 | 12/1988 | European Pat. Off. . |
| 0385809 | 9/1990 | European Pat. Off. . |
| 0403300 | 12/1990 | European Pat. Off. . |
| 0500209 | 8/1992 | European Pat. Off. . |
| 0679650 | 11/1995 | European Pat. Off. . |
| 3701459 | 7/1987 | Germany . |
| 19511269 | 10/1995 | Germany . |
| 87/03781 | 7/1987 | WIPO . |
| 92/08354 | 5/1992 | WIPO . |
| 93/06089 | 4/1993 | WIPO . |
| 94/21606 | 9/1994 | WIPO . |

OTHER PUBLICATIONS

Colliot et al, Brighton Crop Protection Conference—Pests and Diseases—1992, 2–1, pp. 29–34 (Conference dates Nov. 23–25, 1992).

Proc.–Beltwide Cotton Conference 1996, vol. 2, 1996, pp. 759–765 (Hamon et al).

Database WPI, Derwent AN 95–371084 (abstract of JP 07252106 of Oct. 3, 1995).

Database WPI, Derwent Abstract No. 93–212737 (abstract of SU 1746978 of Jul. 15, 1992).

*Primary Examiner*—Allen J. Robinson
*Attorney, Agent, or Firm*—Burns, Doane, Swecker & Mathis, L.L.P.

[57] ABSTRACT

A method for controlling flies infesting mushrooms or expected to infest mushrooms comprising applying to the locus where the insects are or are expected to be an effective amount of a compound of the formula

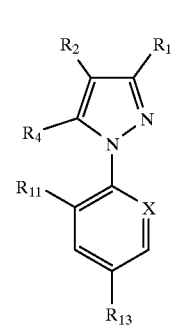

(I)

wherein the substituents are defined in the specification, preferably the compound 5-amino-3-cyano-1-(2,6-dichloro-4-trifluoromethylphenyl)-4-trifluoromethylsulfinylpyrazole.

A method for cultivating mushrooms comprising impregnating the covering or casing layer which is used for the cultivation of mushrooms upon the bottom or feeding layer with an effective amount of a compound of formula (I), preferably 5-amino-3-cyano- -1-(2,6-dichloro-4-trifluoromethylphenyl)-4-trifluoromethylsulfinylpyrazole.

24 Claims, No Drawings

METHOD FOR CONTROLLING FLIES INFESTING MUSHROOMS BY USING A N-ARYLPYRAZOLE OR A N-HETEROARYLPYRAZOLE COMPOUND

This application is a 371 of Pct/EP96/02317, filed May. 30, 1996.

Many insecticides have been described in international patent applications WO 87/3781, 93/6089, 94/21606, and European patent application EP 295,117. However, this prior art does not teach how to protect mushroom cultivations against the flies which are able to infest them. Actually, there is a real and specific need to control flies infesting mushrooms, especially those of the Diptera order and of the families Sciaridae, Phoridae and Cecidae, and possibly other, while making no damage to mushrooms or as little as possible. Various insecticides have been used and have some efficacy, but none are satisfactory and none meets all the growers desires.

Insects from the families Sciaridae, Phoridae and Cecidae are often particularly troublesome in the cultivation of mushrooms. At the present time, it is necessary to apply different insecticides to the cultivation area of mushrooms to control pests from each of these three families. Before the invention, no single insecticide able to control these three families was available in the mushroom Industry. Moreover, compounds used in this invention have also been found to be active against insects resistant to pyrethroid, cyclodiene and organophosphate insecticides and especially effective against the insecticide resistant Sciaridae and Phoridae which are currently difficult to control. Among the Sciaridae family, the species Lycoriella Mali is especially a source of trouble. Among the Phoridae family, the species Megasella Halterata is especially a source of trouble. Among the Cecidae family, the species *Heteropeza pygmae* and *Mycophila barnesi* are especially a source of trouble. These insect pests make the mushrooms unfit for sale and/or reduce the yield of production and/or are vectors for transmission of other diseases, so that, anyway, they are much damageable.

An object of the present invention is to provide a method of control of flies infesting mushrooms which have not the inconveniences of the known insecticides which are used by growers.

Another object of the present invention is to provide a method of control of flies infesting mushrooms which is as little toxic as possible for mushrooms.

Another object of the present invention is to provide a method of control of flies infesting mushrooms which does not require many or multiple applications of active ingredients, as the known insecticides.

Another object of the present invention is to provide a method of control of flies infesting or expected to infest mushrooms, said method using a single application of insecticidally active material up to the time of the harvest.

Another object of the present invention is to provide an effective method of control of flies infesting mushrooms at the various development stages of these insects, including the larvae.

Another object of the present invention is to provide an effective method of control of flies infesting mushrooms which does not require a direct application of the active ingredient to the mushrooms. This is a substantial advantage as far as it substantially reduces the risk of toxicity or of the presence of toxic residues in the mushrooms used as food.

Another object of the present invention is to provide an effective method of control of Diptera flies infesting or expected to infest mushrooms, said method being compatible with commercial mushroom production or systematic mushroom cultivation.

Another object of the present invention is to provide a method of control of flies infesting mushrooms or expected to infest mushrooms, those mushrooms being cultivated mushrooms and/or mushrooms which are used as human food, especially:

those of the Agaricus family, including *Agaricus bisporus*, the oyster mushrooms, which are also known are *pleurotus* spp. the Shiitake mushrooms, also known as Lentinus edodes, the paddy straw mushroom also known as *Valvariella volvacea*.

It has now been found that these objectives can be met partially or totally according to the instant invention and by means of the methods of control as described in the instant specification.

This invention is directed to a method of control of flies infesting mushrooms or expected to infest mushrooms whereby an effective amount of an arylpyrazole compound of formula (I) is applied to the locus where the insects are or are expected to be.

This invention is also directed to a method of control of flies infesting mushrooms or expected to infest mushrooms whereby an effective amount of a compound of formula (I) is applied to the soil where the mushrooms are grown up.

This invention is also directed to a method of control of Diptera flies infesting mushrooms or expected to infest mushrooms which are of one or more of the families Sciaridae, Phoridae and Cecidae, especially those species as here above already indicated.

This invention is also directed to a method of control of flies infesting mushrooms or expected to infest mushrooms whereby an effective amount of a compound of formula (I) is applied or brought into contact or administered to the insects to be controlled.

The effective amounts in the instant specification are insecticidally effective amounts.

In the instant invention, the compounds of formula (1) are those who have the formula:

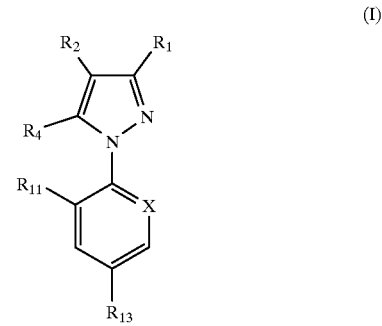

wherein:
R$_1$ is CN or methyl;
R$_2$ is S(O)$_n$R$_3$;
R$_3$ is alkyl or haloallyl;
R4 is selected from the group comprising a hydrogen atom, a halogen atom, and a radical which may be —NR$_5$R$_6$, C(O)OR$_7$, —S(O)mR$_7$, alkyl, haloalkyl, —OR$_8$, or —N═C(R$_9$)(R$_{10}$); R$_4$ is preferably a amino group, which is unsubstituted or which bears one or two substituents selected from the group consisting of alkyl, haloallyl, acyl and alkoxycarbonyl;
R$_5$ and R$_6$ are independently selected from a hydrogen atom, alky, haloalkyl, —C(O)alkyl, C(O)OR$_7$, —S(O)$_r$CF$_3$;

or $R_5$ and $R_6$ form together a divalent radical which may be interrupted by one or more heteroatoms;

$R_7$ is selected from alkyl or haloalkyl;

$R_8$ is selected from alkyl, haloallyl or the hydrogen atom;

$R_9$ is selected from the hydrogen atom and alkyl;

$R_{10}$ selected from phenyl or heteroaryl that is optionally substituted by one or more hydroxy, a halogen atom, —O—alkyl. -S-alkyl, cyano. or alkyl or combinations thereof;

X is selected from the Nitrogen atom and the radical C—$R_{12}$;

$R_{11}$ and $R_{12}$ are independently selected from a halogen atom or the hydrogen atom;

$R_{13}$ is selected from a halogen atom, haloalkyl, haloalkoxy, —S(O)q$CF_3$—, $SF_5$, preferably from a halogen atom, haloalkyl, haloalkoxy, —$SF_5$;

m,n,q,r are independently selected from 0,1, and 2;

provided that when $R_1$ is methyl, then $R_3$ is haloalkyl, R4 is $NH_2$, $R_{11}$ is Cl, $R_{13}$ is $CF_3$, and X is N.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include —$CF_3$ and —$OCF_3$.

A preferred group of 1-phenylpyrazoles for use in the present invention are those of formula (I) wherein:

$R_1$ is CN; and/or $R_4$ is —$NR_5R_6$; and/or $R_5$ and R6 are independently selected from the hydrogen atom, alkyl, haloalkyl, —C(O)alkyl, C(O)O$R_7$; and/or X is C-$R_{12}$; and/or $R_{13}$ is selected from a halogen atom, haloalkyl, haloalkoxy, or —$SF_5$, and $R_2$, $R_3$, $R_7$, $R_{11}$, $R_{12}$ and n are as defined above.

Specific pyrazole derivatives usable in the method falling within the scope of the present invention include 5-amino-3-cyano-1-(2,6dichloro-4-trifluoromethylphenyl)-4-trifluoromethylsulfinylpyrazole. This especially preferred compound for use in the present invention is hereafter called compound A.

The preparation of compounds of formula (I) can be effected according to any process described in International Patent Publications No. WO87/03781, WO93/06089 and WO94/21606, as well as in European Patent Publications numbers 0295117. 0403300. 0385809 and 0679650, German Patent Publication 19511269 and U.S. Pat. Nos. 5,232, 940 and 5,236,938.

Cultivation of mushrooms is a process which may vary from country to country, but there are some general lines in common which are indicated thereafter. The "soil" where the mushrooms are growing comprises basically two parts, or two layers. The bottom layer is a layer which provides essentially the feeding substrate to the mushroom, and the upper layer, which is also called casing layer or covering layer, makes an isolation of this bottom layer from the atmosphere, even though it is not a total and tight isolation.

The bottom layer is often made of a compost, which might comprise, for example, a wet fermented straw, optionally partially compressed so as to reach a density which might be somewhere in between 50 and 150 kg/$m^2$, preferably 95 to 110 kg/$m^2$. This bottom layer may be 3 to 50 cm thick preferably 10 to 25 cm thick. This bottom layer may be thus considered as a feeding layer for the mushrooms. Thus the words bottom layer or feeding layer or compost are practically designating the same thing.

The covering layer comprises generally peat moss which might be mixed with various material, such as limestone, sugar beet residues, compost. The precise composition of this casing layer is not well defined and is part of the general knowledge of the mushroom farmers. This layer is deemed to be a protective layer as well as it is deemed to control or limit the gas exchanges with the atmosphere, even though its precise role may be not well determined. This casing layer is tinner than the bottom layer, and is generally a few centimetres thick, for example 1 to 10 cm, preferably 3 to 7 cm thick.

In the process of cultivating mushrooms, the bottom layer is generally inoculated with the mushrooms fungi or spawn (which is the vegetative stage of the fungus). This inoculation is also known as spawning operation. Then, in a first stage, the inoculated bottom layer, or feeding layer, is held at a warm temperature so as to have the fungi growing, but without having any appearance of a mushroom. This period of growing without a true and visible mushroom may be as long as 1 to 4 weeks. It may be shorter or longer; a 2 weeks period is generally proper.

After that, the covering layer is laid down upon this bottom layer or feeding layer, and the mushroom may then appear and be harvested when deemed proper, the harvesting period May continue during several weeks.

The cultivating method may, as already said, vary from place to place, according to the local practice, the specific mushrooms which are cultivated, the local conditions and the like.

The methods of treatment of mushrooms by application of the insecticidally active material of formula (I) may be made at any time, either in (or on) the bottom layer or on (or in) the covering layer, or on the growing mushrooms. However, according to a particular feature of the instant invention, there has been found a method of cultivating mushrooms whereby the covering layer or casing layer which is used for the cultivation of the mushroom upon the bottom or feeding layer, is a layer which is impregnated with the active ingredient of formula (I). According a feature of the instant invention, this impregnated layer is made either by spraying the said layer after it has been laid down, or preferably the impregnated layer is made by mixing the ground material which normally constitutes the covering layer with a proper formulation of the compound of formula (I), and this mixture is laid down as a global covering layer. This method or process of the invention is particularly advantageous and particularly effective for several reasons:

an even distribution of the compound of formula (I) is highly desirable, at least more desirable with those compounds than with other insecticides, the mushroom which is grown up is not put in direct contact with the insecticidally active material, so that the risk of improper residue in the food is minimised, the amount of insecticidally active material which has to be used is minimal and minimised, the risk of appearance of resistance to insecticide is minimised by elimination of any zone of unlethal amount of insecticide (this happened with organophosphorous compounds as well as with pyrethroids, at least in certain countries).

Thus the invention is also directed to a method of cultivation of mushrooms whereby a single application or introduction of compound of formula (I) is made in the said covering or casing layer, and no further application of insecticide is made at any time up to the end of the harvesting nevertheless a good protection of the mushrooms is obtained.

The precise effective amount of compound of formula (I) may vary rather much according to the intensity of infestation by pest or according to the specific species or conditions. However, the effective amount doses are often comprised in a range of from 1 to 300 mg of compound of formula (I) per kilogram of casing or covering layer, preferably in a range from 5 to 150 mg/kg, and more preferably from 10 to 50 mg/kg. Another way to express these doses is that the effective amount is generally comprised in a range between 40 to 12000 mg of compound of formula (I) per square meter of cultivated area, preferably in a range from 200 to 6000 mg/m$^2$, and still more preferably from 400 to 2000 mg/m$^2$.

The invention finally concerns the use of a compound of formula (I) in mushroom industry.

The formulation which can be used for compounds of formula (I) may be all kinds, especially of suspensions, provided that the said compound is evenly distributed in the material. It is very convenient to have the casing or covering layer mixed with an aqueous suspension of said compound of formula (I). The prior art describes formulations of compounds of formula (I).

The following examples are given to illustrate the invention but should not be considered as limiting it.

EXAMPLE 1

A compost made of fermented straw is inoculated with grains of mushrooms spawn (Agaricus bisporus). The mixture is compressed so as to make a 15 cm thick layer of density 100 kg/m$^2$. This mixture is held 2 weeks at 25° C.

Flies (*Lycoriella mali* and *Megasella halterata* and *Heteropeza pygmae* and *Mycophila barnesi*) were released in the atmosphere surrounding the compost one day before the covering of the compost by mean of the covering layer as here after described. This corresponds to a severe infestation.

Then a covering or casing layer is prepared by mixing a neutralised peat moss (neutralisation is made by mean of grounded limestone) with an aqueous suspension of compound A (125 litres of water for 3.2 g of said compound). This aqueous mixture is poured unto the neutralised peat moss in a mixing container, and the new mixture is applied or laid down as covering layer on the compost. This covering layer is about 5 cm thick so as to get 0.8 g/m$^2$ of compound A. The mushrooms are harvested after 15 to 18 days and harvest continues for 3 to 5 weeks. Results are observed visually:

a small number of flies continue to breed in the compost
no infestation is seen in the covering layer no damage is visible on the mushrooms no insects dwell in the mushrooms Similar experimentation was made without compound A. It ends up with large insect population breeding both in the casing layer and on the mushrooms so as to make them unfit for sales or consumption. Yield is anyway decreased by 10%.

Similar experimentation was made with Dimilin and Diazinon as insecticidally active ingredient. Diazinon is neither effective on Sciaridae nor on Phoridae. Dimilin has poor activity on Cecidae (yield less than 50 % of the yield obtained with compound A).

65 days after spawning, the Phoridae number is 10 times less with Compound A than with similar growing with chlorfenvinphos or tiflumuron.

EXAMPLE 2

Example 1 is repeated with double doses. Similar results are obtained with a slightly reduced yield (5 %).

What is a claimed is:

1. A method for controlling Diptera flies of the family Sciaridae, Phoridae or Cecidae in mushrooms, said method comprising applying to said mushrooms or to the locus in which they grow an insecticidally effective amount of the compound 5-amino-3-cyano-1-(2,6-dichloro-4-trifluoromethylphenyl)4-trifluoromethylsulfinylpyrazole sufficient to control said flies in said mushrooms.

2. A method according to claim 1, wherein said compound is applied to the soil in which said mushrooms grow.

3. A method according to claim 1, wherein said compound is applied to said flies at said locus.

4. A method according to claim 1, wherein from 40 and 12000 mg of said compound are applied per square meter of cultivated area.

5. A method according to claim 1, wherein from 200 to 6000 mg of said compound are applied per square meter of cultivated area.

6. A method according to claim 1, wherein from 400 to 2000 mg of said compound are applied per square meter of cultivated area.

7. A method for cultivating mushrooms in a medium comprising two layers, said layers consisting of a bottom layer comprising feeding substrate which is inoculated with mushroom fungi or spawn, and an upper covering layer, said method comprising impregnating said covering layer with an insecticidally effective amount of the compound 5-amino-3-cyano-1-(2,6-dichloro-4-trifluoromethylphenyl)-4-trifluoromethylsulfinylpyrazole sufficient to control Diptera flies of the family Sciandae, Phoridae or Cecidae.

8. A method according to claim 7, wherein said covering layer is impregnated with said compound by spraying said layer after it has been laid down.

9. A method according to claim 7, wherein the material for said covering layer is mixed with said compound, and the resultant mixture is laid down as said covering layer.

10. A method according to claim 7, wherein said covering layer is impregnated with said compound only once and no farther application of insecticide is made at any time up to the end of harvesting.

11. A method according to claim 8, wherein said covering layer is impregnated with said compound only once and no further application of insecticide is made at any time up to the end of harvesting.

12. A method according to claim 9, wherein said covering layer is impregnated with said compound only once and no further application of insecticide is made at any time up to the end of harvesting.

13. A method according to claim 7, wherein the amount of said compound is from 1 to 300 mg per kilogram of said covering layer.

14. A method according to claim 7, wherein the amount of said compound is from 5 to 150 mg per kilogram of said covering layer.

15. A method according to claim 7, wherein the amount of said compound is from 10 to 50 mg per kilogram of said covering layer.

16. A method according to claim 7, wherein the amount of said compound is from 40 to 12000 mg per square meter of cultivated area.

17. A method according to claim 7, wherein the amount of said compound is from 200 to 6000 mg per square meter of cultivated area.

18. A method according to claim 7, wherein the amount of said compound is from 400 to 2000 mg per square meter of cultivated area.

19. A method according to claim 10, wherein the amount of said compound is from 1 to 300 mg per kilogram of covering layer.

20. A method according to claim 10, wherein the amount of said compound is from 5 to 150 mg per kilogram of said covering layer.

21. A method according to claim 10, wherein the amount of said compound is from 10 to 50 mg per kilogram of said covering layer.

22. A method according to claim 10, wherein the amount of said compound is from 40 to 12000 mg per square meter of cultivated area.

23. A method according to claim 10, wherein the amount of said compound is from 200 to 6000 mg per square meter of cultivated area.

24. A method according to claim 10, wherein the amount of said compound is from 400 to 2000 mg per square meter of cultivated area.

* * * * *